(12) United States Patent
Rice

(10) Patent No.: US 6,691,557 B1
(45) Date of Patent: Feb. 17, 2004

(54) ANALYSIS METHOD FOR LIQUID-FILLED ELECTRIC EQUIPMENT

(76) Inventor: Norman Rice, 472 Belmont Park Dr., Munroe Falls, OH (US) 44262-1736

( * ) Notice: Subject to any disclaimer, the term of this patent is extended or adjusted under 35 U.S.C. 154(b) by 0 days.

(21) Appl. No.: 09/974,355

(22) Filed: Oct. 10, 2001

Related U.S. Application Data

(63) Continuation of application No. 09/810,934, filed on Mar. 16, 2001, now abandoned.
(60) Provisional application No. 60/190,442, filed on Mar. 17, 2000.

(51) Int. Cl.$^7$ .......................... G01N 15/02; G01N 30/00
(52) U.S. Cl. .................... 73/53.07; 73/53.01; 73/61.71; 73/61.72; 73/61.42; 324/71.4
(58) Field of Search ............... 73/53.01, 53.07, 73/61.42, 61.71, 61.72; 324/71.4, 204

(56) References Cited

U.S. PATENT DOCUMENTS

| | | | |
|---|---|---|---|
| 3,619,072 A | * 11/1971 | O'Hara et al. .............. 250/343 |
| 4,402,211 A | 9/1983 | Sugawara et al. |
| 4,502,320 A | 3/1985 | Sakai et al. |
| 4,506,960 A | * 3/1985 | Waggoner et al. .......... 359/391 |
| 4,625,923 A | * 12/1986 | Fishgal ..................... 184/6.21 |
| 4,925,627 A | * 5/1990 | Johnson .................... 422/100 |
| 4,961,845 A | * 10/1990 | Dawson et al. ............ 184/108 |
| 5,071,527 A | 12/1991 | Kauffman |
| 5,194,910 A | * 3/1993 | Kirkpatrick et al. ........ 250/573 |
| 5,210,704 A | 5/1993 | Husseiny |
| 5,271,263 A | 12/1993 | Gibeault |
| 5,313,824 A | 5/1994 | Herguth et al. |
| 5,377,531 A | * 1/1995 | Gomm ..................... 340/457.4 |
| 5,506,501 A | 4/1996 | Fogel et al. |
| 5,508,624 A | 4/1996 | Chon et al. |
| 5,517,427 A | 5/1996 | Joyce |
| 5,531,129 A | 7/1996 | Thornton et al. |
| 5,572,320 A | * 11/1996 | Reintjes et al. ............. 356/246 |
| 5,586,161 A | 12/1996 | Russell et al. |
| 5,604,441 A | 2/1997 | Freese, V et al. |
| 5,614,830 A | 3/1997 | Dickert et al. |
| 5,659,126 A | 8/1997 | Farber |
| 5,674,401 A | 10/1997 | Dickert et al. |
| 5,691,706 A | 11/1997 | Butler et al. |
| 5,739,916 A | 4/1998 | Englehaupt |
| 5,754,055 A | * 5/1998 | McAdoo et al. ............ 324/553 |
| 5,811,664 A | 9/1998 | Whittington et al. |
| 5,817,928 A | 10/1998 | Garvey, III et al. |
| 5,824,889 A | 10/1998 | Park et al. |
| 5,834,642 A | 11/1998 | Decain et al. |
| 5,852,404 A | 12/1998 | Amini |
| 5,889,683 A | 3/1999 | Ismail et al. |
| 5,936,715 A | * 8/1999 | Shapanus et al. ........... 356/70 |
| 6,085,576 A | * 7/2000 | Sunshine et al. ........... 340/634 |

FOREIGN PATENT DOCUMENTS

| | | | |
|---|---|---|---|
| JP | 01041859 A | * | 2/1989 |
| WO | WO-10/20323 | * | 3/2001 |

* cited by examiner

*Primary Examiner*—Edward Lefkowitz
*Assistant Examiner*—Michael Cygan
(74) *Attorney, Agent, or Firm*—Hahn Loeser + Parks LLP

(57) ABSTRACT

The present invention is directed to a method for analyzing the maintenance status of liquid-filled electric equipment. An accurate indication of the maintenance state of an electric device and its insulating liquid is obtained using an analysis method comprising a particle analysis of suspended particles and sediment contained in the liquid. The analysis method can further comprise a chemical analysis of the insulating liquid. This analysis results in profiles of the liquid that give an accurate indication of the maintenance state of the electric device.

13 Claims, 12 Drawing Sheets

ANALYSIS METHOD FOR LIQUID-FILLED ELECTRIC EQUIPMENT

This application is a continuation of application Ser. No. 09/810,934, filed Mar. 16, 2001, now abandoned, which claimed the benefit of provisional application serial No. 60/190,442, filed Mar. 17, 2000.

TECHNICAL FIELD

The present invention is directed to a method for analyzing the maintenance status of liquid-filled electric equipment.

BACKGROUND OF THE INVENTION

The use of liquid-filled power transfer equipment is widespread in the electrical utility industry. These devices, including but not limited to transformers, load tap changers, tap changers, circuit breakers, off-load tap changers, on-load tap changers, switches, and the like, are usually filled with a dielectric insulating liquid.

Operational faults and the resulting degradation of insulating dielectric liquid occuring during the operation of liquid-filled electric power transfer equipment in the electrical utility industry are typically detected using a dissolved gas analysis technique. The presence of certain dissolved gases in the insulating liquid may indicate operational faults such as arcing, pyrolysis, corona discharge, and the like as well as leakage and other contamination. Typical gas analysis techniques can indicate the presence of gases including hydrogen, oxygen, nitrogen, carbon monoxide, carbon dioxide, methane, ethane, ethylene, acetylene, propane, and propylene. FIG. 1 illustrates a general testing protocol typically used in the electric utility industry to monitor the insulating liquid in electric power transfer equipment. In particular, the presence of hydrocarbon gases may indicate degradation of the insulating liquid filling the device, possibly due to electric discharges such as arcing or corona discharge, and consequent breakdown of the insulating capacity of the liquid. In addition to dissolved gas analysis, other tests are typically done to analyze the liquid, including tests to indicate moisture, interfacial tension, acid number, color, qualitative sediment, dielectric breakdown, power factor, and oxidation inhibitor content.

While these tests, along with the dissolved gas analysis, give a quantitative indication of the state of the insulating dielectric liquid, the test results generally do not give a good indication of the maintenance condition of the electric device. In particular, equipment breakdown indicated by operational faults such as arcing and corona discharge, and resulting deterioration of the equipment components, is not directly indicated by the presence of dissolved gases in the insulating liquid. Previous attempts to determine the equipment status include the use of atomic emission spectroscopy to measure the presence of trace metal contaminants in the insulating liquid. Trace metal analysis does not, however, give an accurate indication of the equipment condition. It would, therefore, be desirable to have an analysis method capable of accurately indicating the state of electric power transfer equipment, including the maintenance condition of the various equipment components.

SUMMARY OF THE INVENTION

It has now been found that an accurate indication of the maintenance state of an electric device and its insulating liquid is obtained using an analysis method comprising a particle analysis of suspended particles and sediment contained in the liquid. The analysis method can further comprise a chemical analysis of the insulating liquid. It has been surprisingly found that this analysis results in profiles of the liquid that give an accurate indication of the maintenance state of the electric device.

It is, therefore, an object of the present invention to provide a method of evaluating a liquid from a liquid-filled electric device, comprising the steps of:

obtaining a sample of said liquid; and determining a particulate profile of said liquid, said particulate profile comprising a plurality of predetermined particulate characteristics.

This and other objects and advantages of the invention will become apparent to one of ordinary skill in the art upon reading the following specification and claims.

DESCRIPTION OF THE INVENTION

Figure 1:
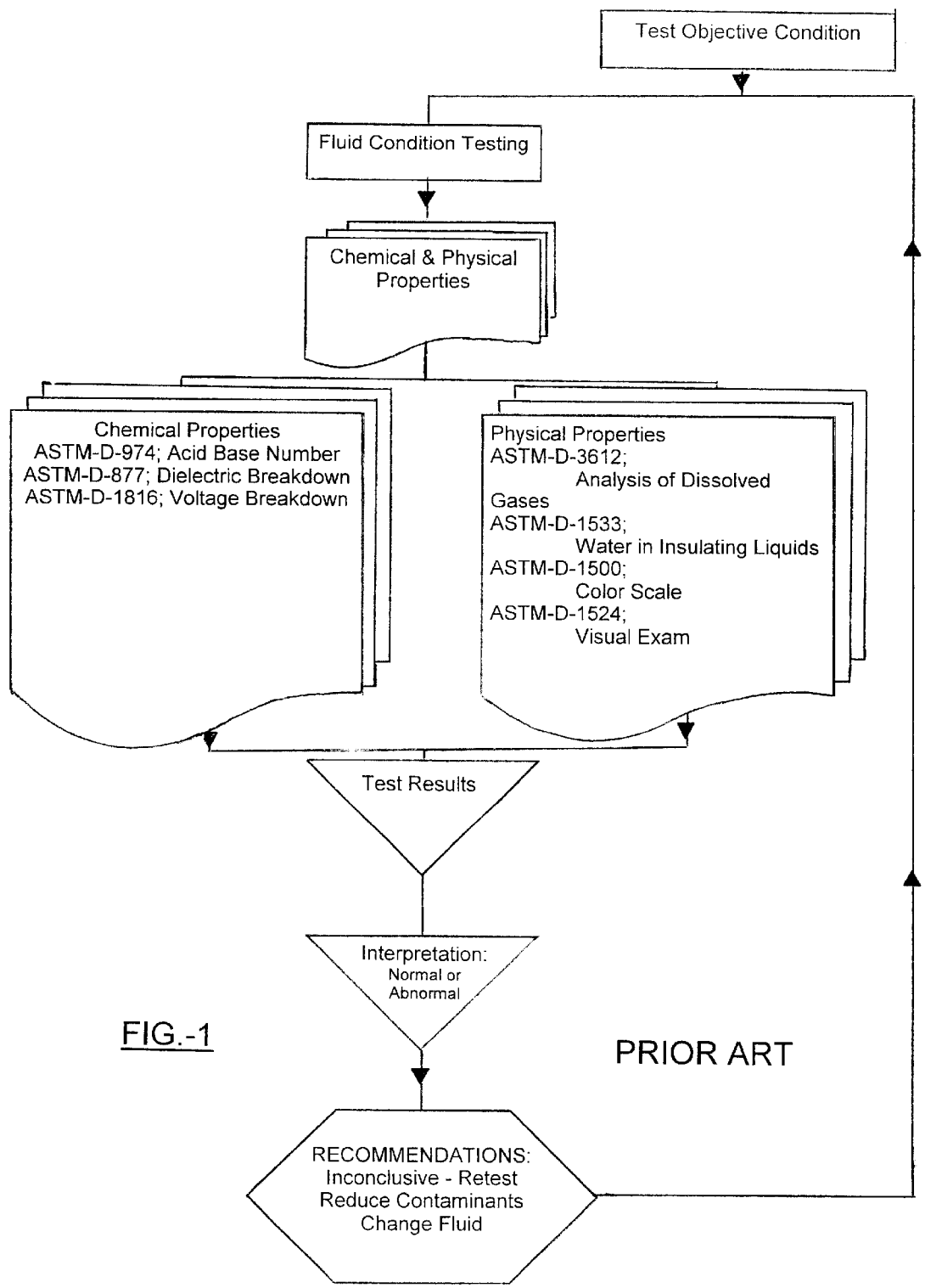
FIG. 1 is a schematic diagram of a prior art testing protocol for electric power transfer equipment and insulating liquid.
Figure 2A:
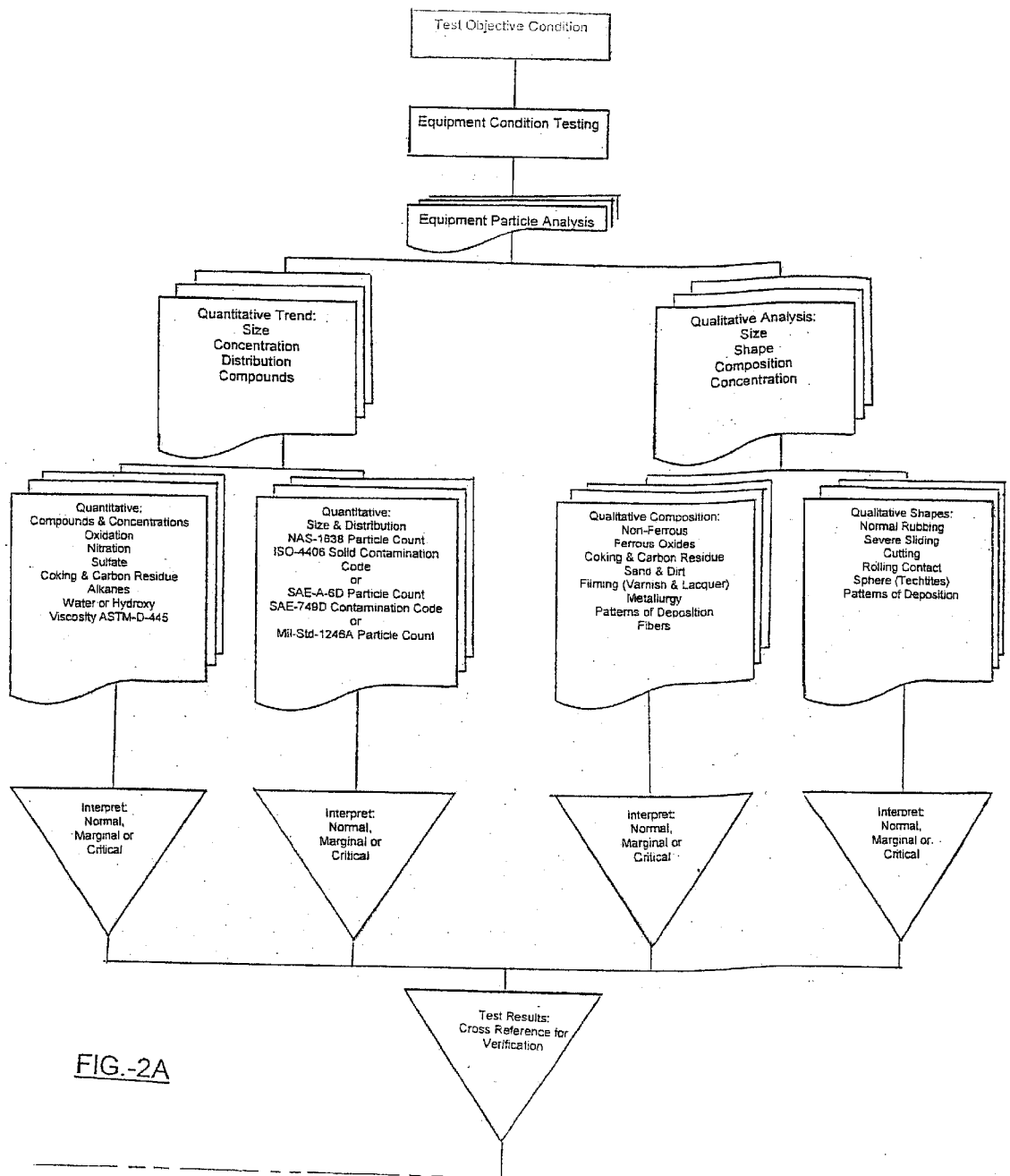
FIG. 2 is a schematic diagram of the methods of the present invention.
Figure 2B:
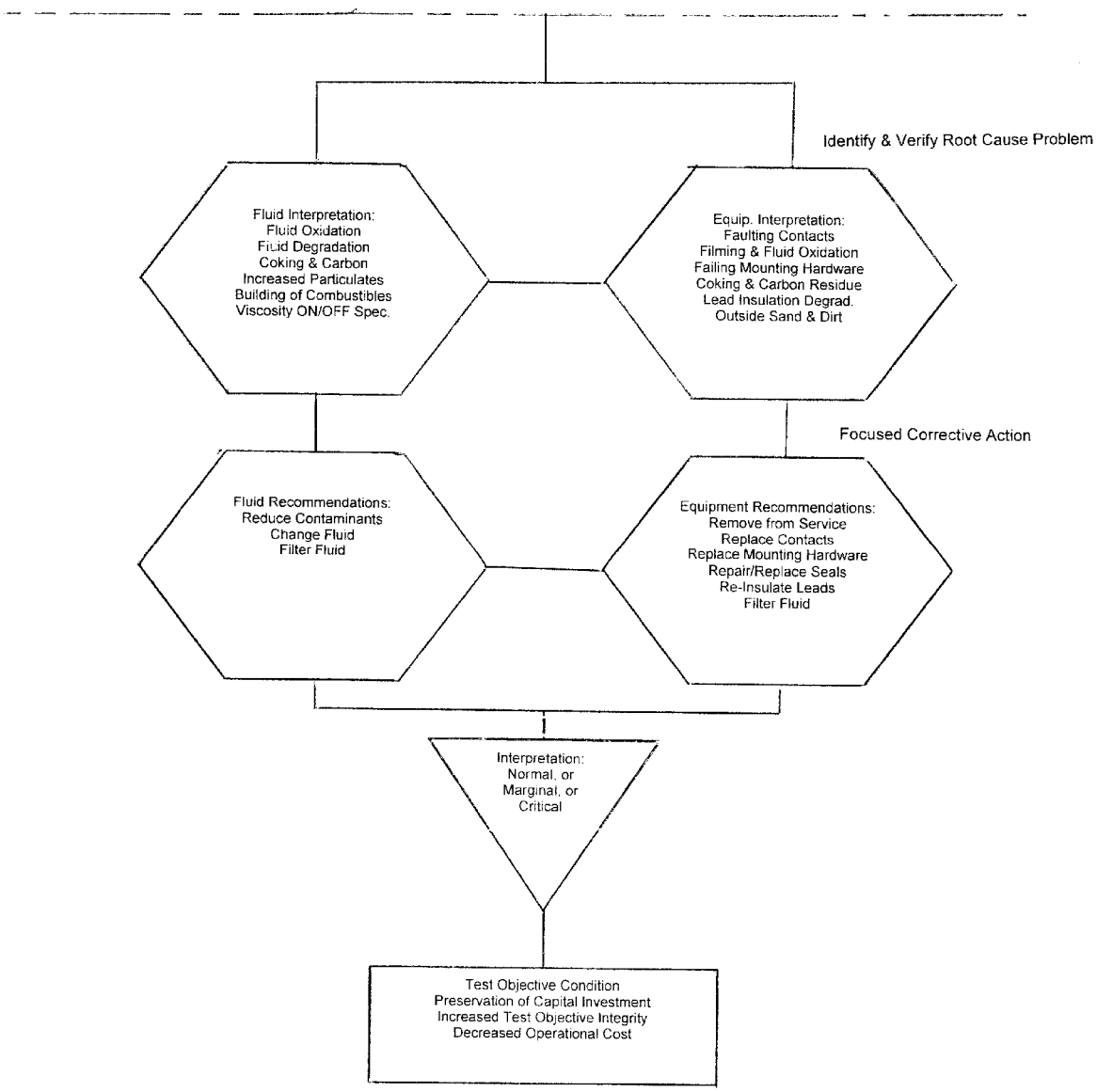

It has now been found that an accurate indication of the maintenance state of a liquid-filled electric device and its insulating liquid is obtained using an analysis method comprising a particle analysis of suspended particles and sediment contained in the liquid. The analysis method can further comprise a chemical analysis of the insulating liquid. It has been surprisingly found that this analysis results in profiles of the liquid that give an accurate indication of the maintenance state of the electric device. A schematic diagram of one testing protocol embodiment of the present invention is illustrated in FIG. 2. The methods of the present invention are applicable to electric power transfer devices commonly used in the electric utility industry, including but not limited to to transformers, load tap changers, tap changers, circuit breakers, off-load tap changers, on-load tap changers, switches, and the like. The methods of the present invention are also applicable to other dielectric insulating liquid-filled electrical devices including but not limited to x-ray equipment and electric discharge machines and the like.

Insulating dielectric liquids used in electric devices include hydrocarbon, silicon, and synthetic fluids. Non-limiting examples of these liquids are DIALA® from Shell, the Exxon UNIVOLT® line, and the Calumet CALTRAN® line.

Insulating dielectric liquid in an electric device, upon use, may contain particulate matter from various sources. A certain amount of particulate loading, without knowledge of the specific nature of the particulates, may be viewed as normal, and the time interval between liquid changes or filtering may be a considerable period; a liquid may not be changed for the entire lifetime of an electrical device. The insulating liquid is clean and substantially particulate free upon charging into the device; however, upon exposure to the high temperatures, electric stresses, and contamination of the interior of the device, the liquid may become loaded with an amount of particulate matter. In one aspect of the invention, the amount of various particulates in the insulating liquid is determined. The presence of various contaminants can indicate the potential for serious operational problems developing in the electric device. Identification of particulate contaminants can may allow identification of fault processes including but not limited to filming, faulting, corona discharge, sparking, overheating, and arcing, and degradation of insulating liquid and electric device components including but not limited to electrical contacts, leads, seals, and mounting hardware. The detection and identification of contaminant particles using both qualitative and quantitative techniques may indicate a fault condition in the electrical device that may not be detected otherwise. This particle analysis, and further in conjunction with the identification of chemical components of the insulating liquid, is useful as a cross-confirmation of the indication of the source of particulate and liquid component contamination. Without the methods of the present invention, a liquid sample containing an amount of unidentified particulate might be viewed by an electric device user as within acceptable limits, whereas a particle analysis of the same liquid sample might indicate the presence of specific particle types indicating probable equipment problems.

Characterization of the particulate loading of a insulating liquid can be done using any of various particle counting techniques, including but not limited to laser extinction, laser scattering, gravimetric analysis, patch counting, optical counting, flow decay, electro-conductivity, and direct reading ferrography. The ASTM-D-785 gravimetric method involves a specific volume of liquid passed through a filter membrane of known pore size following by weighing of the residue. Patch counting involves dispensing a known amount of liquid through a filter membrane of specific pore size. The remaining debris is viewed in a sectored area and amounts are interpolated for various size ranges. Optical particle counting involves trapping magnetic particles by blocking out a light source opposite the particle flow on a large particle and small particle channel. Flow decay involves dispensing a known amount of liquid through a filter membrane or a specific pore size. The procedure measures the time differential between the start and end of a flow cycle. Electro-conductivity involves measurement of the electrical charge accumulated in a metallic filter medium containing a known amount of liquid. Particle characterization made be done by any of these or other particle analysis techniques that are well known in the art, and is reported using the ISO 4406 solid contamination code derived from the NAS (National Aerospace Standards)-1638 particle count.

Along with particle count characterization, the present invention utilizes a qualitative identification of particle types using any of various techniques. In general, particles from an insulating liquid sample are separated from the liquid using ferrography, a magnetic separation and identification technique. Ferrous particles are magnetically deposited on a viewing slide and view under an optical microscope. Extremely small particle (<5 micron) typically lost in particle counting techniques are retained along with the larger sizes. Various particle types are characterized visually using optical microscopy.

A typical ferrographic substrate consists of a glass medium substrate with a non-wetting or antimigration barrier applied to the substrate. The barrier controls the flow of a solution of insulating liquid sample and fixer perpendicularly, with respect to the horizontal plane, between the north and south poles of a high gradient magnet. The substrate is placed at a small angle in relation to the magnet's horizontal surface. The particles contained in the insulating liquid are removed from the liquid and affixed to the surface of the substrate by gravimetric and adhesive forces. The insulating liquid sample is adjusted with a fixer solution to improve particle separation. Following particle separation, excess insulating liquid is rinsed with additional fixer solution.

Where the insulating liquid/fixer solution enters or contacts the ferrographic substrate, large particles (>25 microns) separate from solution first due to the high gradient magnetic attraction, or by gravity. At this point, as the particles are deposited on the substrate qualitative testing begins. The testing subjects all particles to the high gradient magnetic field. This magnetic field will discriminate magnetic and non-magnetic particles. Magnetic particles including all ferromagetic, paramagnetic and diamagnetic particles align in relation to the high gradient magnetic field. The high gradient magnetic field induces separation of magnetic particles in a size range of 0.1 to 800 microns with sufficient separation and distribution to identify the particles' size, shape, composition and concentration.

The use of a high gradient magnetic field in ferrography controls the patterns of deposition of particles by size and composition. Discrimination by particle size allows a specific starting place for observation and verification that the particle deposit technique was properly performed. Larger particles are typically closer to the entry end of the substrate. Non-ferrous metal can be expected to be seen through out the entrie distance of the substrate. This distribution of non-ferrous metal particles also permits a cross reference for verification of particle type.

Distribution of the liquid solution on the nonpermeable substrate surface significantly reduces the amount of lost qualitative information, as compared with filtration techniques. The particles are examined using a compound bi-chromatic microscope at 100×, 200×, 500×, and 1000× magnification. The use of reflected and transmitted light with color filters and polarization allows discrimination of metal from non-metal particles. This discrimination of particles then permits the classification of particles by size, shape, concentration and composition along with the development of a cause and effect relationship with respect to various predetermined particle types. The concentration of particles may be determined by ferrography or other particle analysis technique, and is designated as the equipment particle count, or EPC, as the number of particles in a given sample size.

Of the various particulate types that may be present as contaminants in insulating liquid, several may be identified as to their indication of potential equipment or liquid problems. These particulate types include material generated inside and outside of the electric device. Particulates generated inside of an electric device include those generated through wear and oxidation of internal components under the influence of thermal or electrical stresses, seal degradation, and process contamination. Particulates generated inside of an electric device include but are not limited to rubbing particles, severe sliding particles, cutting particles, rolling contact particles, spheres (also known as techtites), non-ferrous and ferrous oxide particles, coking and carbon residue, filming residue, and paper from wire and lead insulation. Particles generated outside an electric device may include sand, dirt, fiber, welding flux, carborundum dust, metal chips, and the like.

In general, electrical power transfer devices comprise internal components that are largely stationary in operation. Some intermittent motion of internal components occurs, but the internal electrical contact surfaces are generally stationary. For example, in a load tap changer, the reversing switch and its associated electrical contacts may remain in the same position for days or weeks, followed by a single, slow rotation in the switch. Such intermittent motion would not be expected to generate a high concentration of wear particles in the insulating liquid. However, the presence of such particles including rubbing, sliding wear, rolling, and cutting may indicate misalignment or other abnormalities in these intermittently moving parts.

Non-wear particles present in the insulating liquid in an electric power transfer device may be generated as the result of electrical and or thermal abnormalities in the device or liquid. Spheres or techtites, filming compounds, carbon or coke, paper, ferrous oxides, and tempered metals may be present as a result of electrical abnormalities and/or elevated temperatures.

Metallic particles present in the insulating fluid may originate from degradation of internal components either due to wear, electrical abnormalities, or high heat. Internal components of an electric power transfer device such as a load tap changer may include those shown in Table 1, with typical materials of construction indicated for the various components. As indicated by the various materials of construction in Table 1, metallic particles present in insulating fluid may comprise any of several metals including ferrous metals; white non-ferrous metals including nickel, silver, tungsten, molybdenum, aluminum, chromium or titanium; and copper or copper alloys. The presence of a particular metallic particle, then, may be indicative of degradation of a particular internal component of the electric device.

TABLE 1

Internal Components of Load Tap Changer

| Component | Metallurgy | Description |
| --- | --- | --- |
| shaft | ANSI-4340 or ANSI-12214 | medium alloy steel (stress proof) high carbon steel |
| internal mounting bolts | ANSI-303 or ANSI-316 | stainless steel |
| contacts and knife | silver plated tungsten copper alloy | white non-ferrous metal white non-ferrous metal non-ferrous |
| striking plate | copper alloy | non-ferrous |

Figure 5:
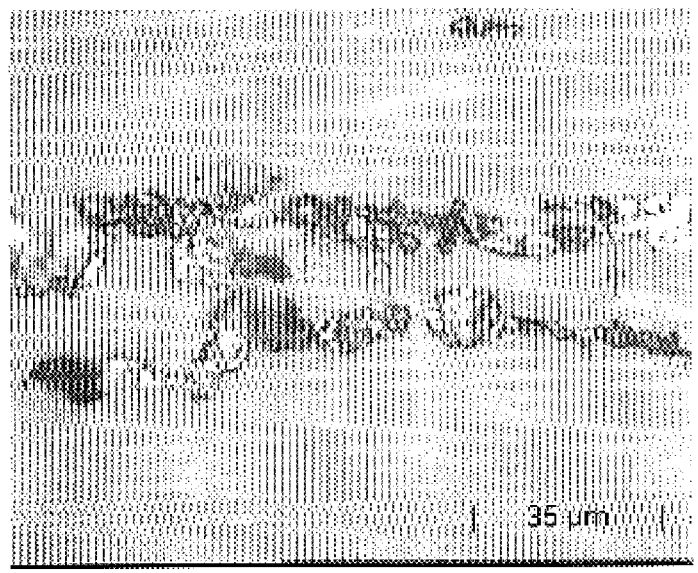
FIG. 5 is a photograph of rubbing particles isolated from an insulating liquid using ferrography.

Normal rubbing particle generation is characteristic of moving surfaces in contact. Normal rubbing particles are flat, platelet particles generally in the 5 micron range or smaller and can range up to 15 microns before being considered a significant problem. Typical rubbing particles are shown in FIG. 5. Normal rubbing particles show no visible texture or striations in the surface of the particles and may be 1–2 microns in thickness with about a 10:1 aspect ratio with respect to the length. Normal rubbing particles may be indicative of excess wear of contact parts or may be the result of break-in wear for new machine components. Rubbing particles resulting from break-in wear may exhibit distinguishing characteristics such as machining marks.

Figure 6:
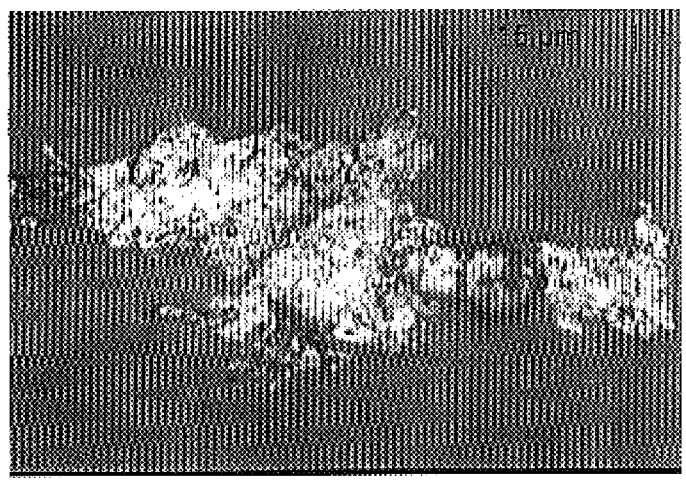
FIG. 6 is a photograph of sliding wear particles isolated from an insulating liquid using ferrography.

Severe sliding particles may be formed by two-body contact and are characterized by parallel striations in the particle's surface as shown in FIG. 6. Sliding particles are about 20 micron and greater with about a 5:1 or less aspect ratio. Severe sliding contact may indicate high heat generation from metal to metal contact in the form of tempering.

Figure 7:
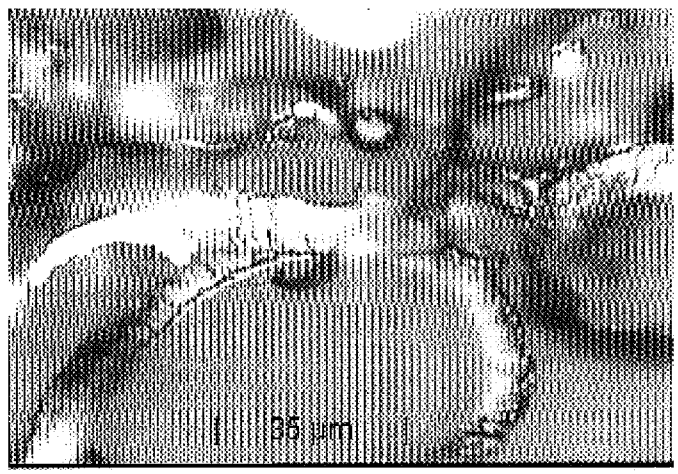
FIG. 7 is a photograph of cutting particles isolated from an insulating liquid using ferrography.

Cutting particles as shown in FIG. 7 are similar in morphology to metal swarfs generated from a machining lathe, except on a microscopic scale. Cutting particles appear as whittling chips or gouged-out curls and may be formed as the result of two- or three-body interference contact, and range in size from about 20 microns to several hundred microns. Two-body wear cutting particles may form as the result of a misalignment of internal components in an electric device. The misshaped or deformed component cuts or plows into a softer or equally hard surface generating these particles. Three-body interference cutting particles typically result from contamination embedded in one relatively soft surface, acting as a tool to cut or plow at another contacting surface.

Figure 8:
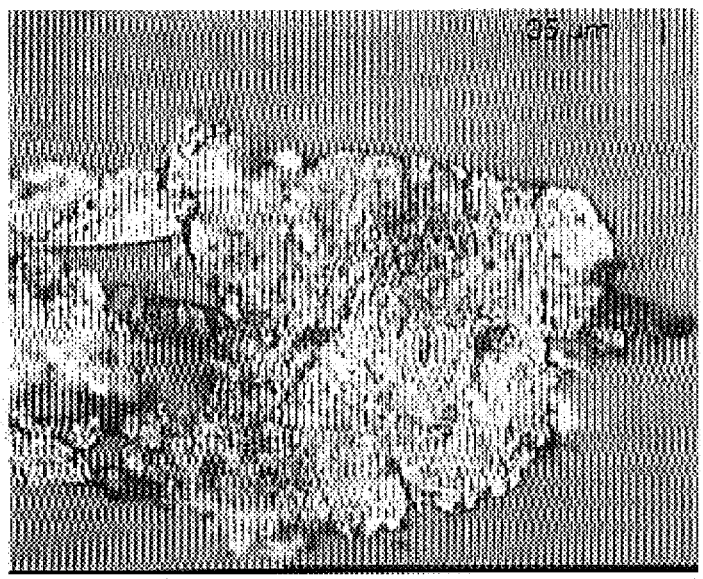
FIG. 8 is a photograph of rolling contact wear particles isolated from an insulating liquid using ferrography.

Rolling contact particles, also called laminar particles or bearing particles, form as the result of relatively large, about 25 micron or larger particles passing between either a stationary and a rolling contact surface combination, or two rolling contacts. Rolling contact particles are shown in FIG. 8. The resulting effect on the particle is reminiscent of pastry dough, rolled thin and flat until the resulting particle has a major dimension to thickness aspect ratio of about 30:1 or greater. Rolling contact particles may be indicative of an abnormal electrical contact mode, such as a spall popping out from a load zone where the electrical contacts are forced against the striking plate surface. Severe sliding interference particles may accompany rolling contact particles in such instances.

Figure 4:
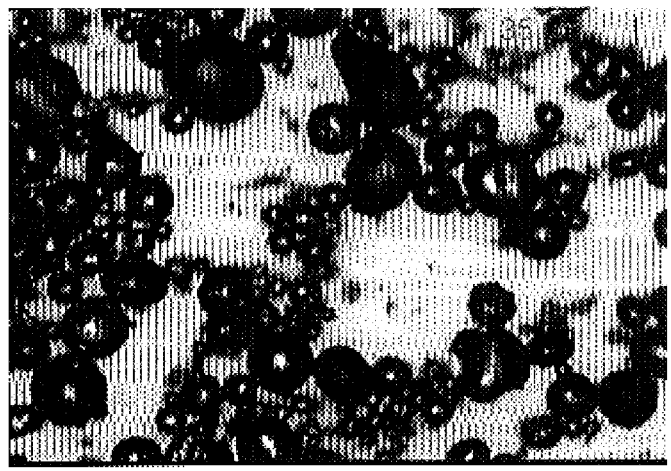
FIG. 4 is photograph of techtite particles isolated from an insulating liquid using ferrography.

Spherical particles, also called techtites, may be found in two forms, either as a wear related particle or a non-wear related particle. Spherical particles are shown in FIG. 4. Wear related spheres may form as fatigue cracks in a loaded surface of internal components of an electric device. As microcracks work through a surface a spall begins to form, the spall may isolate and detach from the surface, generating small, about 5 micron or smaller ferrous spheres with oxidized surfaces. Spherical particles, when present in an insulating liquid may be present in large concentrations and have a relatively uniform size distribution. Non-wear related spheres or techtites may form from inappropriate electrical charges, filming, faulting, corona, arcing, sparking, overheating, or shorting out in an electric device, and are typically copper or copper alloys or other non-ferrous metals in a size range of about 6 microns to about 12 microns. Spherical particles related to electrical abnormalities may be elongated and are typical seen in high concentrations. The elongated shape may be related to the connection of plasma (electric arc) remaining in contact with the removed material that forms a sphere. Spherical particles are generally hard and abrasive and consequently undesirable. Differentiation between copper or other non-ferrous metals and ferrous spheres in a ferrographic analysis is done by considering the size, shape and magnetic differences between the respective sphere types. Copper spheres are randomly dispersed on the ferrographic substrate due to their nonmagnetic nature, while ferrous spheres are generally aligned with the magnetic field. Copper spheres are generally larger than ferrous spheres, and are slightly elongated.

Figure 9:
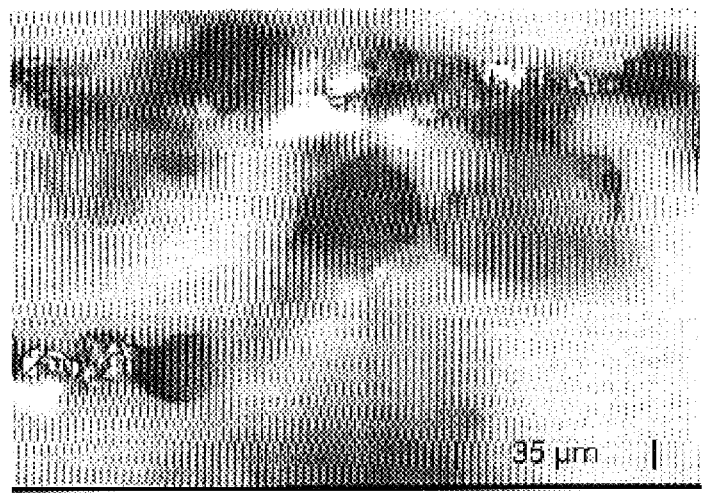
FIG. 9 is a photograph of red oxide particles isolated from an insulating liquid using ferrography.
Figure 10:
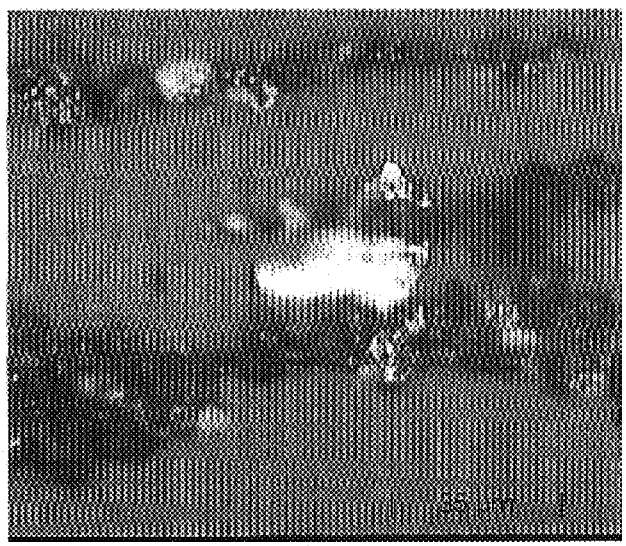
FIG. 10 is a photograph of black oxide particles isolated from an insulating liquid using ferrography.
Figure 11:
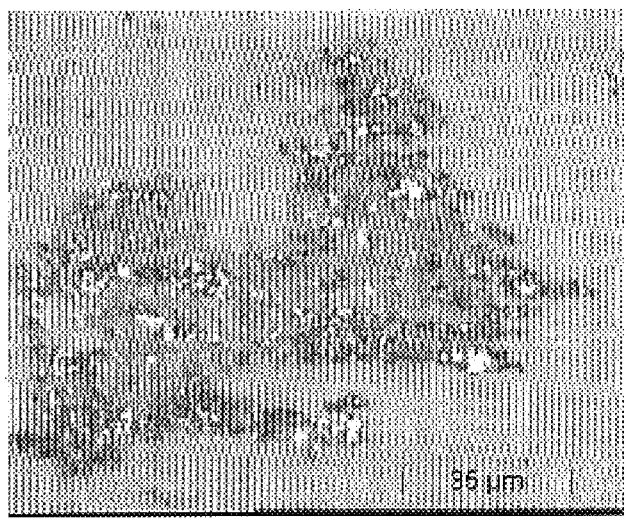
FIG. 11 is a photograph of corrosive particles isolated from an insulating liquid using ferrography.

Non-ferrous and ferrous oxide particles include oxides such as red oxides ($Fe_2O_3$), both the α-type Hematite and β-type or rust as shown in FIG. 9. Black oxides ($Fe_3O_4$) are shown in FIG. 10, corrosive FeO particles are shown in FIG. 11. Ferrous oxide particles when present in insulating liquid may include particles in a size range of from about 0.1 micron to about 5 micron. These small particles are likely undetected due to loss through filters in gravimetric analysis, but are detected using the more sensitive ferrography technique.

Insulating liquids comprise refined hydrocarbons with residual amounts of oxidation compounds, nitrogen compounds, and sulfur derivatives and other impurities. Although paraffinic hydrocarbon liquids have a greater oxidation resistance than other liquids, degradation of the liquid from the effects of electrical stress, heat and metal alloys (e.g. copper and copper alloys) leads to the formation of organic peroxides. The resulting peroxides form alcohols, aldehydes, ketones, and organic acids and subsequent high molecular weight, oil insoluble polymer filming compounds.

Nitration compounds (NOx) are formed when hydrocarbons are burned at high temperatures. The presence and resulting increase in nitration compounds indicate a consumption of the insulating liquid and contribute to the formation of oxidation and filming compounds.

Petroleum sulfonates present in insulating liquid are refinery by-products of the sulfuric acid treatment of "white oils." These sulfonate compounds ($SO_2OX$, where X is a metal ion such as copper or an alkyl radical) react with insulating liquid under the influence of electrical stress, heat and metal alloys to form organic peroxides which contribute to the oxidation process.

Figure 12:
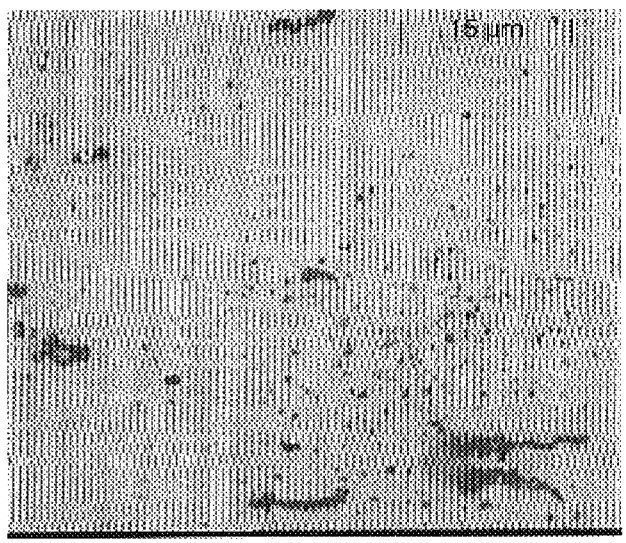
FIG. 12 is a photograph of coking, graphite, and carbon residue isolated from an insulating liquid using ferrography.

Coke and carbon residue may be formed due to pyrolysis of hydrocarbons in an insulating liquid under the influence of thermal and electrical stresses. Carbon residue from an insulating liquid is shown in FIG. 12. The presence of carbon residue in an electric device may have adverse performance effects on the electric device. Coke and carbon residue may be small particles in a size range of about 0.1 micron to about 5 micron.

Figure 13A:
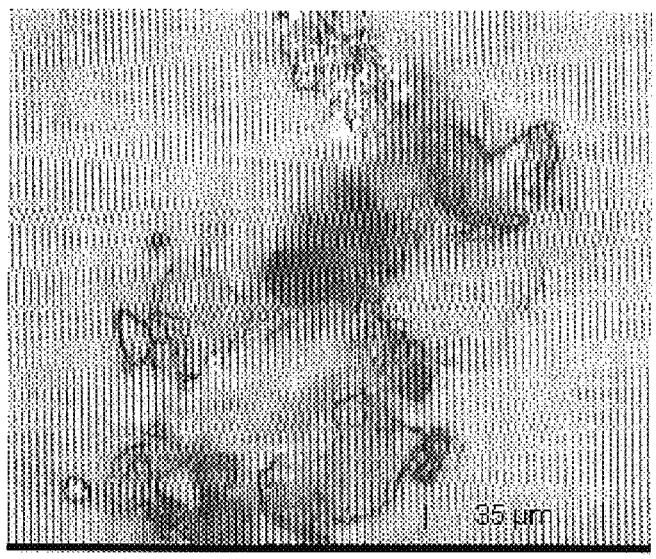
FIGS. 13A, 13B and 13C are photographs of filming residue isolated from an insulating liquid using ferrography.

Filming particles, also characterized as lubricant degradation, friction polymers, varnish, or lacquer may indicate overstress on the insulating liquid in a critical contact area. Filming particles may be the result of polymerization of the insulating liquid under the adverse effects of temperature, pressure and electrical stress in the electric device. One type of filming particle, designated as Phase 1, is a soft varnish or lacquer formed from polymerized alcohols or carboxylic acids, as shown in FIG. 13A. These particles may redistribute into the insulating liquid and may increase the acidity of the insulating liquid, thereby depleting protective additives and contribute to corrosion of internal surfaces of the electric device. Oxidation in the form of this type of varnish or lacquer may increase the viscosity of the insulating liquid, and is an indication of the level of degradation of insulating liquid. The presence of oxidation varnish or lacquer may indicate overstressing, overheating, or depletion of antioxidant additives.

Figure 13B:
Figure 13C:
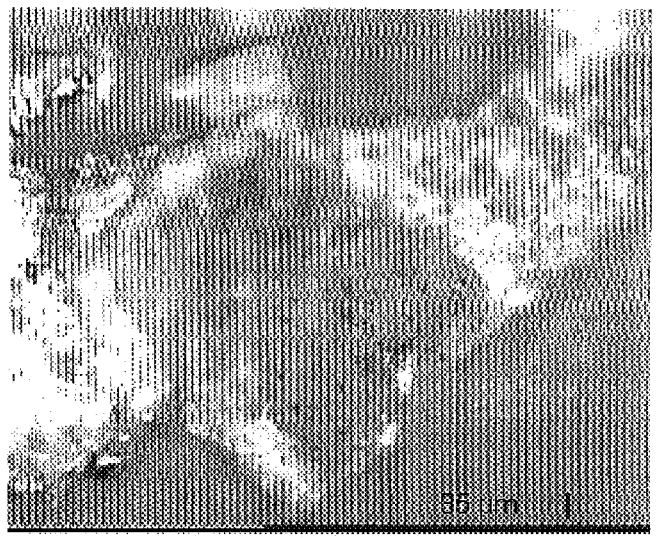
Figure 14:
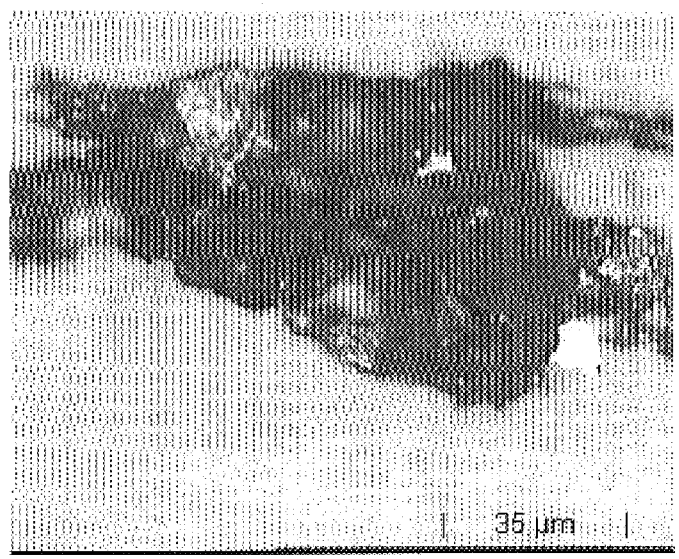
FIG. 14 is a photograph of heat treated particles isolated from an insulating liquid using ferrography.
Figure 15:
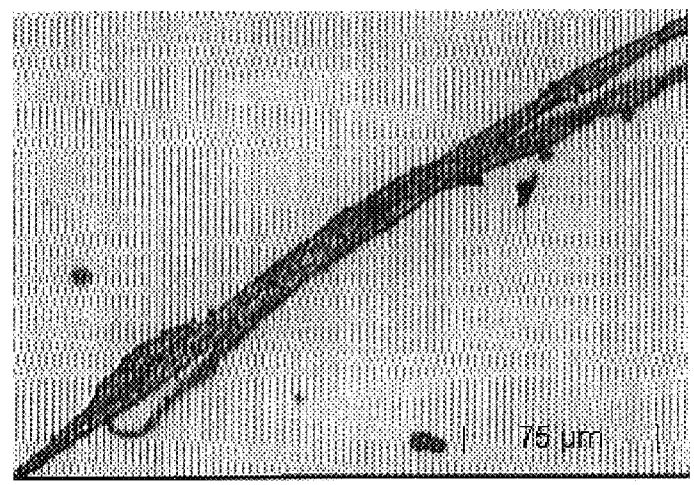
FIG. 15 is a photograph of cellulosic paper fiber isolated from an insulating liquid using ferrography.
Figure 16:
FIG. 16 is a photograph of metallic particles showing characteristic coloring due to heart tempering in an insulating liquid.

FIG. 13B shows filming particles, designated as Phase 2, containing coke or carbon particles suspended in a matrix. These type of filming particles are more rigid that the oxidation varnish and do not redistribute into the insulating liquid. FIG. 13C shows highly rigid filming particles, designated as Phase 3; these type of particles are reflective and are thereby identifiable under reflected light in optical microscopy. Filming particles are typically not detected by conventional quantitative particle techniques due to their transluscent matrix.

Further identification of particle types may be done using heat treatment of a ferrographic sample. Heat treatment provides the ability to categorize particles as to type. Particles are broadly categorized as organic and inorganic. Both types of particles have similar appearance in both unpolarized and polarized light, but organic material will melt, shrivel, char or vaporize and appear less brilliant after exposure to heat. Inorganic particles include various metal particles identifiable by a rainbow coloration at a temperature characteristic of a given alloy. A ferrographic substrate is typically exposed to temperatures in the range of about 330° C. to about 540° C. for 90 seconds. Heat treatment of a ferrographic substrate is done by placing the inorganic substrate on a hot plate at a given temperature and time interval. Subsequent coloration at a given temperature is characteristic of a given alloy, as shown in Table 2. Exceeding the specified temperature or time interval can result in the generation of irreversible oxidation layer formation, which precludes identification by heat treatment.

TABLE 2

Metal Particle Characterization by Heat Treatment

| Test Material | Other Similar Materials | Color | | | |
|---|---|---|---|---|---|
| | | Test 1 330 C. | Test 2 400 C. | Test 3 480 C. | Test 4 540 C. |
| ANSI 52100 | carbon steels and low alloy steels | blue | light gray | | |
| 3.5% Carbon Cast Iron | medium alloy steels approx. 3–8% carbon | straw-bronze | deep bronze some mottled bluing | | |
| Type A Nickel | high nickel alloys | no change | no change | bronze with significant bluing on most particles | all particles blue or blue-gray |
| ANSI 304 Stainless Steel | high alloy steels | no change | generally no change; slight yellowing on some particles | straw-bronze with slight bluing on some particles | most particles still straw-bronze; some particles showing mottled bluing |

Metallic particles isolated on the ferrographic substrate may also exhibit coloration without external heat treatment, due to heat tempering by insulating liquid reaching high temperatures during operation of a electric device. Typically, metallic particles exhibiting coloration due to heat tempering by the insulating liquid indicate undesirably high operating temperatures in the liquid, in excess of about 300° C.

Contaminant particles originating from outside the electric device may be found in the insulating liquid. These particles include natural and synthetic fibrous material from sources such as paper, filters, breather elements, and rag lint. Natural fiber materials are inconsistent in shape and include wool, cotton, paper and other cellulosic material. Synthetic fibers typically appear to be extruded with consistent diameter; these include rayon, dextron, polyester and fiberglass.

Fiber contamination can also originate from inside the electric device. For example, paper insulation on electrical wires and leads can deteriorate under heat and electrical stress. The presence of paper fiber in the insulating liquid may indicate deterioration of such insulation.

Analysis of the ferrographic substrate using optical microscopy and heat treatment to identify the various particle types and concentrations of each lead to the generation of a particulate profile for a given sample of insulating liquid. This profile may then be compared to a standard particulate profile as shown in Table 3. Deviation in the insulating liquid particle profile from the standard profile may indicate undesirable conditions in the electric device and/or the insulating liquid. The comparison may indicate the need for repair of the device or change in the liquid.

TABLE 3

Standard Particulate Profiles

| Component | Marginal | Critical | Indications |
|---|---|---|---|
| Filming | Phase 2 rigidly formed matrix | Phase 3 highly rigid matrix; reflective | Generation of organic peroxides which form alcohols, aldehydes, ketones and organic acids to form the high molecular weight, oil insoluble polymer film compounds reducing the insulating capacity of the insulating liquid. |
| Fibers (paper and other cellulose) | Paper > 0.2% of EPC[1] | Paper > 0.5% of EPC | Deterioration of insulation on electrical leads and seal leakage between transformer and load tap changer |
| Coking | forming matrix | congruent matrix | Reduction in insulating properties of insulating liquid and leading to failure of electrical device contacts |
| Techtites (Spheres) | >0.1% of EPC | >0.9% of EPC | Inappropriate electrical charges, filming, faulting, corona, arcing, sparking, overheating or shorting out of electrical device |
| Fe Rubbing Wear | >10% of EPC | >20% of EPC | Loosening and movement of internal mechanisms as well as mounting apparatus of electrical contacts |
| Oxides | red, black & nonferrous | red, black & non-ferrous | 1. Acidic attack of insulating liquid on electrical device internal components. 2. Presence of moisture which then has been driven off as the result of heat of operation of the electrical device. 3. Equipment leak allowing outside contaminants such as hematite and magnetite to enter electrical device. 4. Elevated operating temperatures during the formation of metal particles |
| tempered metallic particles | ferrous and non-ferrous metal tempering | ferrous and non-ferrous metal tempering | Elevated operating temperatures in liquid |

[1]equipment particle count

Chemical analysis of the insulating liquid in the present invention is performed using one or move known analysis methods. These methods include but are not limited to infrared spectroscopy including Fourier Transform Infrared Spectroscopy (FTIR), mass spectroscopy, gas chromatography, liquid chromatography, wet chemical analysis, atomic absorption spectroscopy, and inductively coupled plasma spectroscopy, and the like. In one embodiment, liquid samples taken from a electric device is analyzed using FTIR to determine the presence and concentration of several components in the liquid which are indicative of undesirable conditions in the insulating liquid and in the electric device.

The insulating liquid contained within an electric device experiences high temperature and electrical stress during operation of the device. This harsh environment, in combination with the exposure of the insulating liquid to the interior surfaces of the device, may lead to at least partial chemical alteration of the insulating liquid as compared with fresh, unused liquid. This chemical alteration of the insulating liquid may be due to phenomena such as thermal degradation and chemical reaction, leading to chemical components indicative of these phenomena. These components include chemical species characteristic of several types of degradation of both the insulating liquid and the electric device. For example, high temperature and electrical arcing can lead to pyrolysis of the hydrocarbon constituents of the insulating liquid, resulting in carbon or coke formation. In addition, longer chain hydrocarbon species in the insulating liquid under the influence of heat and/or electrical arcing or other discharge can be degraded to lower molecular weight species including but not limited to methane, ethane, propane, ethylene, and propylene. One advantage of the chemical analysis of the present invention over prior art dissolved gas analysis for electric devices lies in the ability of the chemical analysis to detect non-volatile degradation products that are not detected using dissolved gas analysis. Detection of nonvolatile components using the methods of the present invention, at concentrations below those detectable by dissolved gas analysis, allows earlier detection of fault conditions in both the insulating liquid and in the electric device.

Hydrocarbon degradation products formed during electrical or thermal stress of the insulating liquid include but are not limited to methane, ethane, propane, ethylene, and propylene. Hydrocarbon degradation products are detectable at 810 cm$^{-1}$ and 765 cm$^{-1}$ in an infrared spectrum of insulating liquid.

Insulating liquid exposed to elevated temperature can oxidize to a variety of compounds, the majority of which as carbonyl compounds, including carboxylic acids. Carboxylic acids and/or alcohols contribute to the acidity of insulating liquid which may make the insulating liquid more corrosive and more viscous. The concentration of oxidation products is an indicator of the level of degradation in the insulating liquid. Increase in oxidation products may indicate overstressing, overheating, or depletion of antioxidant additives caused by over-extended liquid change intervals. The combination of temperature, arcing, and carboxylic acids contribute to the formation and buildup of filming compounds. One indication of the level of oxidation products is detectable at 1720 cm$^{-}$ in an infrared spectrum of the insulating liquid.

Nitrogen oxides produced from the oxidation of nitrogen compounds during electrical stress of the insulating liquid from electrical charges, filming, faulting, corona, arcing, sparking, overheating or shorting out. Nitration increases the viscosity of the insulating liquid and is a major cause of the build-up of varnish or lacquer known as filming compounds. One indication of the level of nitration compounds is detectable at 1640 cm$^{-1}$ in an infrared spectrum of the insulating liquid.

Sulfur oxides are produced by the combustion of sulfur compounds present in refined hydrocarbon products. These oxides react with moisture, also produced by the combustion process, to form acids such as sulfuric acid. The sulfuric acid is neutralized in insulating liquid by basic neutralizing additives to form inorganic sulfates. Sulfur is highly reactive with copper and copper alloys such as brass and bronze as well as other non-ferrous metals. These non-ferrous metals comprise the internal components of an electric device. One indication of the level of sulfate compounds is detectable at 1150 cm$^{-1}$ in an infrared spectrum of the insulating liquid.

Coking, or carbon particles, result from molecular stress and pyrolysis from electrical draw on refined complex hydrocarbon mixtures such as insulating liquid and typically are too small to be removed by filtration. Carbon particle tend to build up until concentrations cause deposition of carbon residue on contact surfaces insides the electric device. Coking or carbon particles are detectable at 3800 cm$^{-1}$ and 1980 cm$^{-1}$ in an infrared specturm of the insulating liquid. Carbon particles can also be determined by thermogravimetric analysis (TGA).

The presence of water in insulating liquid may indicate a leak in the fluid system of the electric device. Such leaks can lead to serious failure of the electric device and early leak detection is desirable to avoid such failure. The presence of water in the insulating liquid is further detrimental to the dielectric strength of the insulating liquid as is therefore undesirable. The presence of moisture can be the result of condensation from an air leak in the liquid reservoir of the electric device or may derive from contamination in the insulating liquid when charged to the device. Water or other hydroxy compounds are detectable at 3400 cm$^{-1}$ on an infrared spectrum of the insulating liquid.

Figure 3:
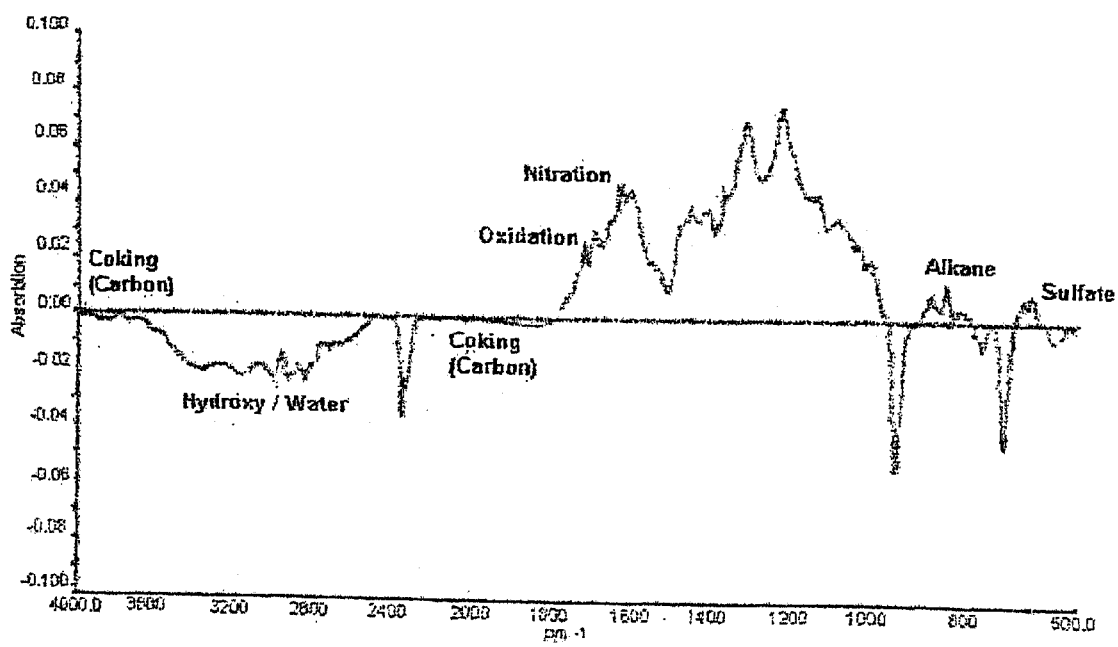
FIG. 3 is a representative infrared spectrum of an insulating liquid sample.

In one embodiment, FTIR spectroscopy is used to determine the presence and concentration of low molecular weight hydrocarbons, nitrates, sulfates, oxidation products, and hydroxyls in the insulating liquid. A typical infrared spectrum of a hydrocarbon-based insulating liquid indicating the presence of various components is shown in FIG. 3.

Analysis of an insulating liquid using the chemical analysis method of the current invention results in a chemical component composition profile including low molecular weight hydrocarbons, oxidation products, nitrates, sulfates, coking (carbon particles), and water. In addition, the viscosity of the insulating oil is also measured further indicating the presence of these some of these components as discussed herein. The composition profile generated by the chemical analysis is compared to a standard composition profile to indicate the possible problems to be identified, both for the insulating liquid as well as for the electric device itself. A standard composition profile is shown in Table 4.

TABLE 4

Standard Composition Profiles

| Component | Marginal | Critical | Indications |
|---|---|---|---|
| Hydrocarbons[1] | .03–8 abs/cm | >0.8 abs/cm | Decomposition of insulating liquid due to high temperature and/or electrical stress |
| Water/Hydroxyls | 0.5–2.0 ppm | >1.0 ppm | Leak in fluid system |
| Oxidation | 0.3–0.5 abs/cm | >0.8 abs/cm | generation of organic peroxides to form filming compounds; reduced insulating capacity of liquid |
| Sulfates | >1.0 | >2.0 abs/cm | reaction with insulating |

TABLE 4-continued

Standard Composition Profiles

| Component | Marginal | Critical | Indications |
|---|---|---|---|
| (Sulfonates) | abs/cm | | liquid; corrosion of copper and copper alloys; formation of peroxides to form filming compounds |
| Nitrates | >0.65 abs/cm | >1.0 abs/cm | reaction with insulating liquid to form filming compounds |
| Coking | 2.4 abs/cm | >2.75 abs/cm | reduced insulating capacity of liquid; possible failure of electrical contacts |
| Viscosity | >±10% of spec. | >+ 20% of spec. | presence of moisture; presence of oxidation and filming compounds; quality control to ensure proper fluid in use |

[1]low molecular weight hydrocarbons e.g. methane, ethane, propane, ethylene, propylene In an alternative embodiment, analysis and evaluation of a dielectric insulating liquid may be done using an on-line analysis technique. Rather than sampling the liquid for an off-site analysis in a laboratory or other remote location, apparatus can be utilized to sample and identify particulate materials using computerized image analysis techniques with a means to direct a sample of liquid to an automatic sampling means, and comparison of acquired images of particles to standard particle images in a database.

Figure 17:
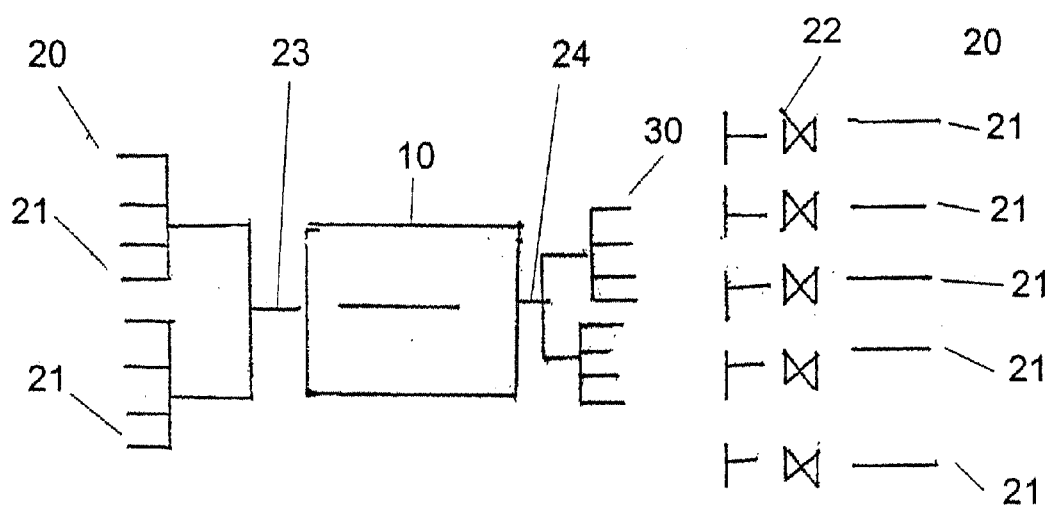
FIG. 17 is a schematic representation of an on-line testing system according to an embodiment of the invention.
Figure 18:
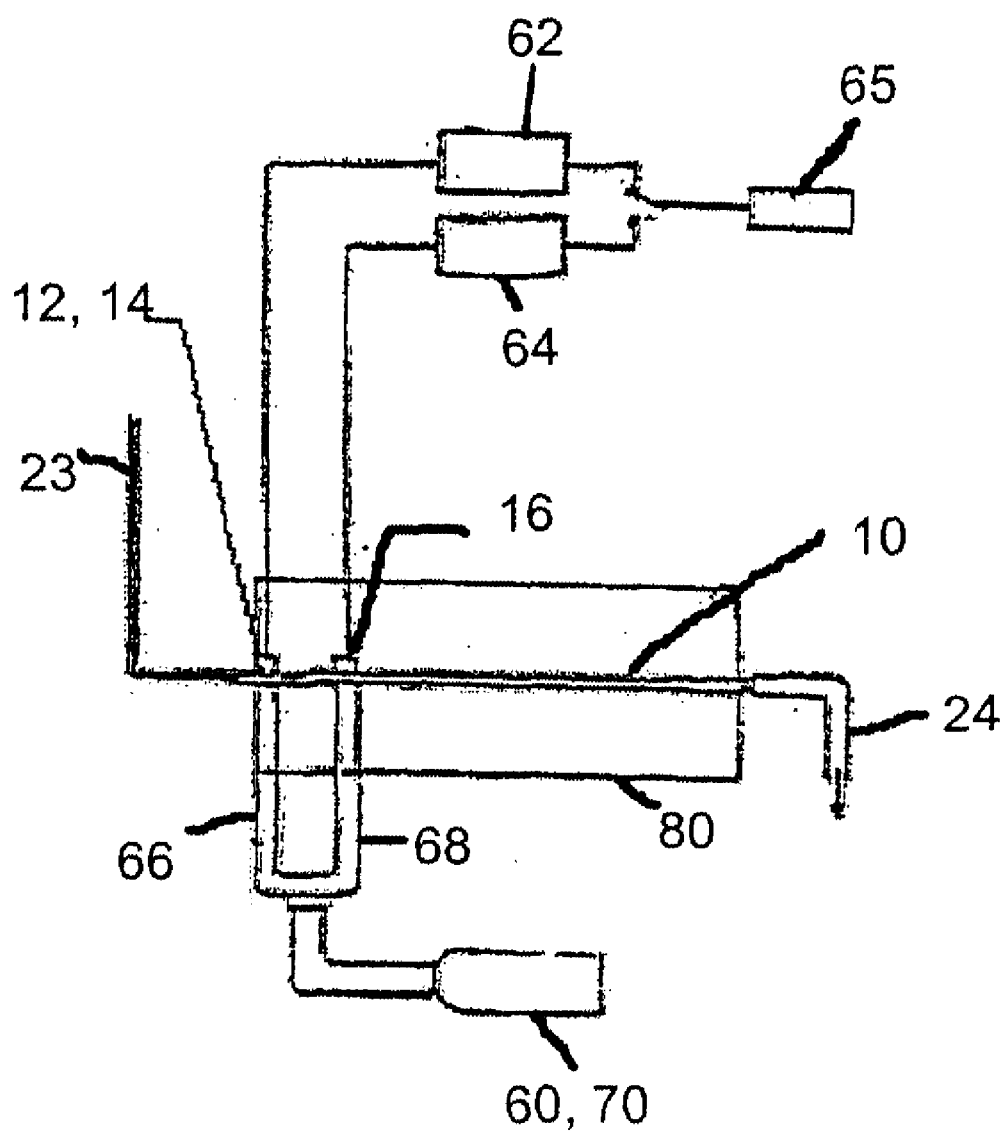
FIG. 18 is a schematic representation of a sample testing system according to the embodiment as shown in FIG. 17.
Figure 19:
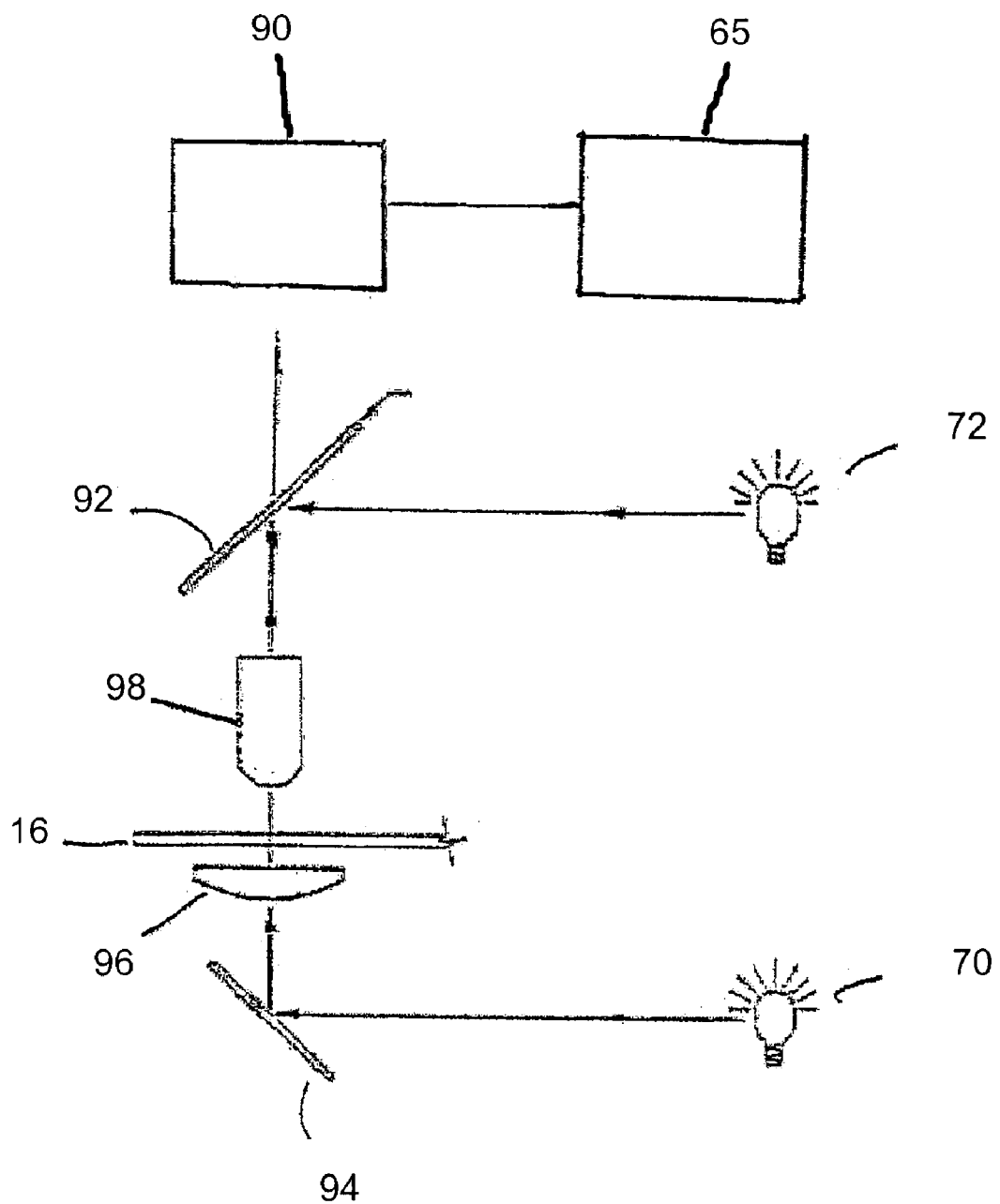
FIG. 19 is a schematic representation of a processing cell associated with the embodiment as shown in FIG. 17.

FIGS. 17, 18 and 19 illustrate one approach to online testing of the present invention. The online system permits multiple continuous online testing with a single instrument at a sub station rather than the generally accepted approach of one instrument per test objective at the substation. FIG. 17 illustrates the chamber 10 and multiple piping configuration of the online testing method and instrument.

It is to be understood that test objectives include but are not limited to electrical power transmission and distribution (T&D) equipment such as transformers (T), load tap changers (LTC), tap changers (TC), circuit breakers (CB), oil filled circuit breakers (OCB), off-load tap changers (OLTC) and on-load tap changers (IOLTC) and electric discharge machines (EDM), shall be referred to as the Testing Objectives (TO).

Online testing using the methods of the present invention requires a somewhat larger and significantly more technical sophisticated. Three separate but integrated evaluations may be performed simultaneously. These evaluations are as follow:

1. Particle Count (Solid Particles/Laser Diode)
   a. Size
   b. Distribution
   c. Concentration
2. Compound Evaluation (Interferometer)
   a. Coking
   b. Oxidation (organic acids)
   c. Nitration
   d. Sulfate
   e. Alkanes (volatiles)
   f. Moisture
3. Particle Types (Optical/Bi-Chromatic)
   a. Composition (Metal v.s. Non-Metal)
      i. Metallurgy (Ferrous v.s. Non-Ferrous)
   b. Size & Distribution
      i. NAS-1638 or ISO Ranges
   c. Shape
      i. Rubbing & Harmonic Fatigue
      ii. Severe Sliding
      iii. Cutting & Plowing
      iv. Rolling Contact Use of one radiation source (i.e. laser) resolves two aspects of this expansion of the online system. The radiation source can be utilized in succession fro both the compound evaluation as well as the particle count.

The online analyzer is centrally located in the electrical power substation. The TO of interests are plumbed or piped to a central manifold 20. The central manifold 20 is a combination of lines 21 from several TOs with flow either vacuum pumped (for induced flow) or pressure pumped (to force flow) and a check valve system 22. As the pumps are operating they either induce or force circulation of the fluids through the equipment's respective loop. In the case of sealed T&D equipment an inert gas purge is utilized to avoid any accumulation of oxygen that may permit combustion. The check valve systems opens to the TO fluid line 21 of interest or in a predetermined order or in a rotating order, the circulating fluid allows a representative sampling of insulating fluid to enter the processing chamber 10 through inlet line 23 and exit though line 24 for return to the proper TO through manifold 30.

Representative samples of the insulating fluid arrives at the central instrument-processing cell 10. The unitized processing cell consists of three chambers 12, 14, and 16. The processing cell prechamber 12, central chamber 14 and aft chamber 16.

The entire chamber assembly 10 is at an inclined angle (~30°) with respect to the horizontal plane. This inclined angle also provides two functions. The fist function is to allow any air bubbles to flow upward and not be included in the either the laser particle count, disrupt the laser for the interferometer measurements or create false shadows during the image analysis.

The processing cell pre-chamber 12 allows for sufficient flow rate to obtain a particle count. The one laser 60 is split, directed through fiber optics 66 and passes through the representative insulating fluid sample. As particles pass through the laser beam, particles stop transmission of the laser beam to the diode 62 opposite the laser. This interruption in the laser to the diode 62 allows for the measurement of size and concentration of the particles through analysis in processor 65.

The processing of the central chamber 14 utilizes the other portion of the split laser directed through fiber optics 68. This portion of the laser is then divided again for compound evaluation (Interferometry) by FT-IR processing. Then the two parts are recombined again after introducing the path difference. This combined beam goes through the sample to the detector 64 and processor 65. Any interference pattern obtained as the path difference is varied.

For single frequency the pattern is a sine wave with maxima when the two beams are exactly in phase and minima when the two beams are 180 degrees out of phase. The path difference is achieved as the mirror moves causing the beam to go in and out of phase. The signal received at the detector varies producing the sign wave. For a broad band source, the interference pattern is the sum of all of the sine waves for all of the frequencies present. This interferogram consists of a strong signal at the point where the path difference is zero, falling away rapidly on either side. Customary spectrum of energy is as a function of frequency can be obtained from the interferogram by mathematical method of Fourier transformation. When samples are absent, the result is a single-beam spectrum. The overall configuration of which is characteristic of the beam splitter and energy source.

The aft chamber portion 16 of the processing cell 10 is the most complex. Not only does light pass through the portion of the cell but the flow through this portion of the cell is also momentarily suspended. During this time of flow suspension a high gradient electromagnet field is established by electromagnet 80. The establishment of this magnet field allows the discrimination of ferrous metal particle from non-ferrous particles via ferrography. Secondly, a bi-chromatic light source 70, 72 is activated. This bi-chromatic light source consists of both a transmitted source 70 and a reflected source 72. The combination of these source serves two purposes. This first purpose is for further discrimination of metal particles from non-metal particles. The second purpose if the acquisition of a digital image using digital camera 90. The bichromatic light is directed to the fluid sample for ferrographic analysis via optics including mirrors 92 and 94, condenser lens 96 and objective lens 98. An optical image thereby generated is detected by a digital camera 90 for ferrographic analysis in processor 65.

The digital image is analyzed with image analysis & diagnostic software. This diagnostic software essential counts each pixel of the digital image making distinctions between colors and ratios to make determinations of particle, size shape, composition and concentration.

The invention is illustrated by the following non-limiting examples.

EXAMPLES

Example 1

Quantitative Particulate and Chemical Component Analysis

Insulating liquid from an underground load tap changer (LTC) was analyzed for the maintenance state of the device using a combination of chemical and particulate analysis. A sample of insulating liquid (Shell Diala) was taken from the bottom of the LTC reservoir drain and analyzed using FTIR, ferrography, particle count, and optical microscopy. The results of the particle counting and infrared analyses are shown in Table 5. Ferrographic and optical microscopy analysis of the particles indicated the presence of techtites as shown in FIG. 4 and filming compounds as shown in FIG. 13. The presence of copper techtites was indicative of a high degree of contact surface degradation due to arcing in the striking plate of the electrical contact assembly of the reversing switch in the LTC. The maintenance state of the device was rated as critical with recommendation for immediate repair of deteriorated contact mechanism. Post-analysis inspection of the LTC confirmed the severe degradation of the striking plate.

TABLE 5

| Particle Count | | | |
| --- | --- | --- | --- |
| size, microns | number | Misc. Data | |
| 5–15 | 1598 | viscosity[1] | 8.98 |
| 15–25 | 124 | water ppm | <10 |
| 25–50 | 50 | coke | 2.14 |
| 50–100 | 10 | oxides | 0.00 |
| 100+ | 2 | nitrates | 1.73 |

TABLE 5-continued

| Particle Count | | | |
| --- | --- | --- | --- |
| size, microns | number | Misc. Data | |
| EPC | 1784 | sulfates | 0.83 |
| ISO Scale | 18/14 | hydrocarbons[2] | 0.92 |

[1]ASTM-D-115-72 at 40 C
[2]methane, ethane, propane, ethylene, propylene

The invention has been described with reference to various embodiments. Obviously, modifications and alterations will occur to others upon the reading and understanding of the specification. It is intended to include all such modifications and alterations insofar as they come within the scope of the appended claims or the equivalents thereof.

What is claimed is:

1. A method of evaluating the operation of electrical equipment using a liquid, comprising the steps of:
   obtaining a sample of the liquid from the electrical equipment;
   analyzing the liquid for particulate components, including the presence of electrical erosion products, to determine a profile of particulates in the liquid, the profile comprising predetermined particulate characteristics; and
   determining an indication of the operating condition of the electrical equipment by analyzing the particulate profile.

2. The method according to claim 1, wherein the step of analyzing the liquid for the presence of electrical erosion products includes analyzing for the presence of techtites.

3. The method according to claim 1, wherein the step of analyzing the liquid for particulate components further includes analyzing for filming, fibers, coking, techtites, Fe rubbing, oxides and tempered metallic particles.

4. The method according to claim 1, further comprising:
   analyzing the liquid for non-particulate components, including the presence of non-volatile insulating liquid degradation products, to determine a profile of non-particulate components, the profile comprising predetermined non-particulate characteristics.

5. The method according to claim 4, wherein the step of analyzing the liquid for the presence of non-volatile insulating liquid degradation products includes analyzing for the presence of hydrocarbons.

6. The method according to claim 4, wherein the step of analyzing the liquid for non-particulate components includes analyzing for hydrocarbons, water, hydroxyls, oxides, sulfates, coking and viscosity.

7. The method according to claim 4, wherein the steps of analyzing the liquid for particulate components and analyzing the liquid for non-particulate components include determining particle count, particle count distribution, particle count concentration, particle count composition, particle count shape, compound evaluation for coking, oxidation, nitration, sulfate, alkanes and moisture, particle type composition, particle size, and particle shape.

8. The method according to claim 4, wherein the step of analyzing the liquid for non-particulate components comprises at least one chemical analysis method selected from the group consisting of infrared spectroscopy, mass spectroscopy, gas chromatography, liquid chromatography, wet chemical analysis, atomic emission spectroscopy, and inductively coupled plasma spectroscopy.

9. The method according to claim 1, wherein the step of analyzing the liquid for particulate components comprises at least one particle analysis method selected from the group consisting of optical microscopy, laser extinction, ferrography, particle counting, and metal heat treatment.

10. The method according to claim 1, wherein the predetermined particulate characteristics profile include at least one member selected from the group consisting of techtites, rubbing particles, sliding particles, cutting particles, rolling contact particles, ferrous oxides, carbonaceous particles, filming particles, paper, fiber, cellulosics, dirt, sand, and tempered metals.

11. The method according to claim 1, wherein the step of determining an indication of the operating condition of the electrical equipment comprises:

comparing the particulate profile to a standardized particulate profile.

12. The method according to claim 1, wherein the electrical equipment is an electric power transfer device.

13. The method according to claim 1, wherein the electrical equipment is selected from the group consisting of transformers, load tap changers, tap changers, circuit breakers, off-load tap changers, on-load tap changers, switches, x-ray machines, and electric discharge machines.

* * * * *